(12) United States Patent
Krespi et al.

(10) Patent No.: US 9,402,686 B2
(45) Date of Patent: Aug. 2, 2016

(54) DUAL ACCESS SINUS SURGERY METHODS

(75) Inventors: Yosef Krespi, New York, NY (US);
Victor Z. Kizhner, New York, NY (US)

(73) Assignee: Valam Corporation, New York, NY (US)

( * ) Notice: Subject to any disclaimer, the term of this patent is extended or adjusted under 35 U.S.C. 154(b) by 708 days.

(21) Appl. No.: 12/716,561

(22) Filed: Mar. 3, 2010

(65) Prior Publication Data
US 2010/0228227 A1  Sep. 9, 2010

Related U.S. Application Data

(60) Provisional application No. 61/157,030, filed on Mar. 3, 2009.

(51) Int. Cl.
| | | |
|---|---|---|
| *A61B 18/22* | (2006.01) |
| *A61M 25/00* | (2006.01) |
| *A61N 5/06* | (2006.01) |
| *A61B 17/24* | (2006.01) |
| *A61M 25/01* | (2006.01) |
| *A61M 25/10* | (2013.01) |

(52) U.S. Cl.
CPC .............. *A61B 18/22* (2013.01); *A61M 25/00* (2013.01); *A61N 5/0624* (2013.01); *A61B 17/24* (2013.01); *A61M 25/01* (2013.01); *A61M 25/10* (2013.01); *A61M 2025/105* (2013.01); *A61N 2005/0607* (2013.01)

(58) Field of Classification Search
CPC ...... A61B 18/22; A61M 25/00; A61N 5/0624; A61N 2005/0607
USPC .......... 604/500, 506, 513; 606/13, 14, 15, 16, 606/108; 128/898
See application file for complete search history.

(56) References Cited

U.S. PATENT DOCUMENTS

| | | | | |
|---|---|---|---|---|
| 5,711,315 A | * | 1/1998 | Jerusalmy | ............... 128/898 |
| 2005/0107853 A1 | | 5/2005 | Krespi | |
| 2006/0149310 A1 | * | 7/2006 | Becker | ............... 606/196 |
| 2007/0249896 A1 | * | 10/2007 | Goldfarb et al. | ............ 600/101 |
| 2008/0172033 A1 | | 7/2008 | Keith et al. | |
| 2009/0054881 A1 | | 2/2009 | Krespi | |

* cited by examiner

*Primary Examiner* — Theodore Stigell
*Assistant Examiner* — Benjamin Koo
(74) *Attorney, Agent, or Firm* — Joseph P. Aiena

(57) ABSTRACT

A method for sinus surgery includes piercing first and second access openings into the anatomy of a human subject to access an inaccessible sinus site for cooperatively manipulating respective first and second surgical instruments inserted through the openings. One instrument, for example an endoscope, can permit viewing of the sinus site while the other instrument is manipulated to effect a treatment at the sinus site. The maxillary and other sinuses can be accessed and anti-inflammatory and other treatments can be applied. Systems and instruments for performing such sinus surgery methods are also disclosed.

16 Claims, 3 Drawing Sheets

DUAL ACCESS SINUS SURGERY METHODS

CROSS-REFERENCE TO A RELATED APPLICATION

This application claims the benefit of provisional patent application No. 61/157,030 filed on Mar. 3, 2009, the disclosure of which provisional patent application is incorporated by reference herein.

STATEMENT REGARDING FEDERALLY SPONSORED RESEARCH OR DEVELOPMENT (Not applicable.)

The present invention relates to sinus surgery methods and systems and provides novel procedures and systems enabling the an inaccessible sinus site to be accessed with two instruments simultaneously via dual passageways through the subject's anatomy.

BACKGROUND OF THE INVENTION

Sinusitis is a condition affecting over millions of Americans, and large populations in the rest of the developed world. Sinusitis can occur when one or more of the four paired sinus cavities, namely the maxillary, ethmoid, frontal or sphenoid cavities, becomes obstructed. Normally the sinus cavities, each of which are lined by mucosa, produce mucous which is then moved by beating cilia from the sinus cavity out to the nasal cavity and down the throat. The combined sinuses produce approximately one liter of mucous daily, so the effective transport of this mucous is important to sinus health.

Each sinus cavity has an opening into the nasal passage called an ostium. When the mucosa of one or more of the ostia or regions near the ostia become inflamed, the egress of mucous can be interrupted, leading to possible infection of the sinus cavity, or sinusitis. Infections of the maxillary and/or ethmoid sinuses usually make up the majority of cases of sinusitis, with fewer cases implicating the sphenoid and frontal sinuses. Sinusitis can be chronic, persisting for many months or even years.

United States Patent Application No. 2005/0107853 to Krespi discloses methods for broad-spectrum treatment of chronic rhinosinusitis wherein electromagnetic radiative energy including visible, and optionally, thermal RF, microwave or other longer wavelengths, is applied to target internal surfaces of the sino-nasal tract to destroy or incapacitate superficial microorganisms without the use of antibiotics. United States Patent Application No. 2009/0054881 to Krespi discloses process for treatment of biofilm which can be resident in the sino-nasal tract. Described processes include applying mechanical shockwaves to remove, disrupt, disperse, dislodge, destroy or attenuate the biofilm. The shockwaves can be generated in a handheld instrument by impinging a laser on a suitable target material.

United States Patent Application No. 2008/0172033 to Keith et al. describes a method of treating a constricted sinus passageway wherein a visualization tool is passed through a lumen or channel in a cannula and a balloon dilation catheter is deployed through the same cannula to place the balloon within or across the constricted anatomical space. The balloon is then expanded to expand a portion of the constricted anatomical space.

Notwithstanding a wide range of available treatments for sinusitis and chronic sinusitis, it would be desirable to have improved methods and systems for performing surgery at inaccessible sinus sites.

The foregoing description of background art may include insights, discoveries, understandings or disclosures, or associations together of disclosures, that were not known to the relevant art prior to the present invention but which were provided by the invention. Some such contributions of the invention may have been specifically pointed out herein, whereas other such contributions of the invention will be apparent from their context. Merely because a document may have been cited here, no admission is made that the field of the document, which may be quite different from that of the invention, is analogous to the field or fields of the present invention.

SUMMARY OF THE INVENTION

The present invention provides, inter alia, methods of performing sinus surgery at an inaccessible sinus site which provides enhanced visualization of the sinus site.

The present invention also provides, inter alia, methods of performing sinus surgery at an inaccessible sinus site which permits a wide range of instruments to be employed and to be manipulated cooperatively to treat the sinus site.

In one aspect, the invention provides a method of sinus surgery for treating an inaccessible sinus site in a human subject in need of sinus treatment, the method comprising:

piercing a first access opening into the anatomy of the human subject from a first externally accessible anatomical location to provide access to the inaccessible sinus site;

piercing a second access opening into the anatomy of the human subject from a second externally accessible anatomical location to provide access to the inaccessible sinus site;

inserting a first surgical instrument into the first access opening and traversing the first access opening with the first surgical instrument to introduce the first surgical instrument to the inaccessible sinus site;

inserting a second surgical instrument into the second access opening and traversing the second access opening with the second surgical instrument to introduce the second surgical instrument to the inaccessible sinus site; and cooperatively manipulating the first and second instruments while each instrument is introduced to the sinus site to perform a sinus treatment. If desired, the first and second access openings can comprise channels or paths and the channels paths can be cut, drilled, bored or otherwise surgically formed in the subject's anatomy to extend any desired proportion of the distance from the respective first or second anatomical location to the inaccessible sinus or other site.

The first accessible location and the second accessible location can be sublabial sites, optionally sites in the canine fossa or other region of the upper gum. Both the first access opening and the second access opening can extend into or through a maxillary antrum.

If desired, the first surgical instrument can comprise a source of illumination to illuminate the target site and optionally comprises a viewing device enabling the sinus site to be viewed externally of the human subject. The first surgical instrument can comprise an endoscope, optionally a telescopic endoscope.

The method can comprise piercing the second access opening at a convergent angle to the first access opening the first and second openings being oriented to converge at or near the inaccessible sinus site. The angle between the access openings can be selected from the group of angles consisting of an acute angle, an angle in the range of from about 3° to about 60°, an angle in the range of from about 5° to about 30° and an angle in the range of from about 10° to about 20°. The first accessible site has a separation from the second accessible site selected from the group consisting of: a separation of from about 1 mm to about 100 mm, a separation of from about 5 mm to about 50 mm; and a separation of from about 10 mm to about 30 mm.

If desired, the method can comprise piercing the first access opening or the second access opening or both the first and the second access openings with a piercing tool providing an opening having a greatest transverse dimension, in the range selected from the group consisting of from about 0.5 mm to about 5 mm and from about 1 mm to about 3 mm. The first instrument can comprise an endoscope having a transverse dimension of at least 3 mm.

In another aspect, the method can comprise inserting a first hollow sheath into the first access opening, inserting a second hollow sheath into the second access opening and inserting the first and second surgical instruments through the respective first and second sheaths into the respective first and second access openings. If desired, the method can include raising the upper lip of the human subject upwardly and piercing the first and second access openings in the upper gum.

The sinus treatment performed can comprise a therapeutic or prophylactic treatment.

In another aspect, the invention provides a system for performing sinus surgery by a method according to claim 1, the system comprising:
  a piercing tool for forming the first and second access openings in the subject;
  at least two hollow sheaths insertable into the access openings; and
  first and second surgical instruments insertable into the first and second hollow sheaths, respectively, each surgical instrument being manipulable with axial movement along the respective access opening;
wherein the at least two sheaths can be disposed at a convergent angle, one sheath to the other and one or each surgical instrument can be manipulated to move in the respective sheath and opening in a direction transverse to, or angled to the direction of movability of the other surgical instrument in the respective sheath and access opening.

Pursuant to some aspects of the invention, the sinus surgery can be endoscopic and useful procedures, for example, antimicrobial treatments with visible radiation or pharmacologic agents, can be performed via the first and second access passageways, without use of a balloon or a guide wire for a balloon or like device.

BRIEF DESCRIPTION OF THE DRAWINGS

Some embodiments of the invention, and of making and using the invention, as well as the best mode contemplated of carrying out the invention, are described in detail herein and, by way of example, with reference to the accompanying drawings, in which like reference characters designate like elements throughout the several views, and in which.

DETAILED DESCRIPTION OF THE INVENTION

Some examples of surgical methods according to the invention comprise double port maxillary sinus endoscopy and surgical. In such methods, two ports can be punctured or otherwise formed in suitable locations of the subject's anatomy, for example, beneath the upper lip. The inaccessible sinus site can be at, in or near the maxillary sinus, or another desired sinus, and can for example be the maxillary ostium or another sinus ostium. One or both of the first and second passageways can extend transantrally, if desired. Usefully, an endoscope, or other visualization device can be inserted through one of the first and second passageways and a surgical instrument can be inserted through the other passageway. A surgeon or other user can manipulate the endoscope and surgical instrument cooperatively to perform a therapeutic procedure at the sinus site and to visualize the procedure.

By utilizing a separate access passageway for the endoscope, which is non-parallel with the access passageway employed for the surgical instrument, for example convergent therewith, the user has greater flexibility of visualization and instrumentation than would be the case with a dual lumen instrument inserted through a single passageway where both the surgical instrument and the endoscope are on the same axis.

The invention provides surgical systems and methods wherein two separate ports into the anatomy are employed as opposed to using one port with two channels, the two ports give the surgeon two different working axes. Having one working axis for an endoscope and a different working axis for a surgical device can make the procedure more efficient. Using a single port with two lumens, the lumens remain on one axis which is the same for the endoscope and for example a balloon or other surgical device deployed.

Figure 1:
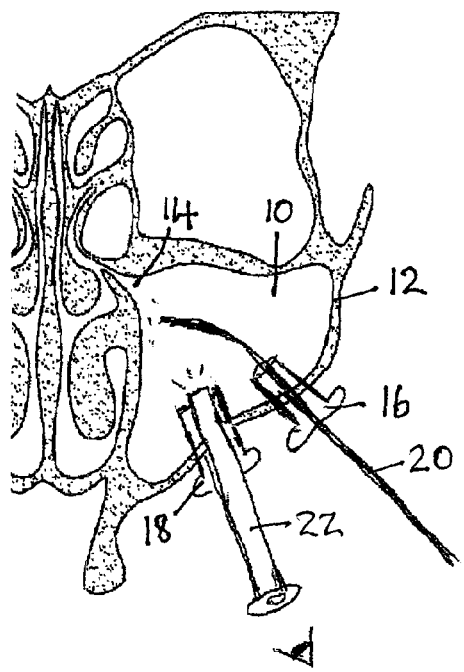
FIG. 1 is a cross-sectional view of a portion of the right-hand side of the skull of a human subject, looking toward the corona, which defines some of the sinus cavities, showing one embodiment of a system for performing sinus surgery according to the invention.

Referring to FIG. 1, some of the bony structure of the skull can be seen. This bony structure defines certain of the sinus cavities, including the maxillary antrum 10 of the maxillary sinus. The maxillary antrum 10 is further defined by the upper jawbone 12 and drains through the maxillary ostium 14

The sinus surgery systems illustrated comprises a first sheath 16 which extends through a first artificial, surgically created opening in jawbone 12 which can be pierced through the canine fossa, or other suitable location above the gum line, by a trocar, a drill, or another suitable piercing instrument (not shown). A second sheath 18 extends through a second artificial surgically created opening in jawbone 12 which can also be pierced through the canine fossa, or other suitable location above the gum line, by a trocar or another suitable piercing instrument (not shown).

Desirably the first and second openings are oriented to have axial directions pointed generally toward maxillary ostium 14. In this example, the axes of the two sheaths 16 and 18 are spaced apart along the jawbone by a distance of about 5 to 10 mm. Usefully, each sheath can have any desired internal diameter up to about 3 or 4 mm each.

Sheaths 16 and 18 can be surgically inserted into the subject using any suitable procedure. For example, the subject can be given a local anesthetic, with or without sedation, prior to making the openings. Local anesthesia, if employed, can be by needle injection into the upper gum, and optionally also adjacent to the target sinus site for example by transnasal injections. For the procedure, the subject can be supine on his or her back or, can be seated in a reclinable chair such as a dental chair. If desired, the subject can be under general anesthesia during part or all of the procedure.

A first, working surgical instrument, for example a laser fiber 20 extends through first sheath 16 in the first opening, into maxillary antrum 10 and is shown with the tip of the laser fiber in the vicinity of maxillary ostium 14. Laser fiber 20 can be an optical fiber connecting externally with a suitable source of laser energy (not shown).

A second, viewing surgical instrument, for example an endoscope 22 extends through second sheath 18 in the second opening, into maxillary antrum 10 and is oriented to point toward maxillary ostium 14. Endoscope 22 can be of any suitable structure permitted by the caliber of sheath 18. For example, endoscope 22 can be rigid, if desired, can be telescopic and can provide illumination. Laser fiber 20 can be manipulated externally to apply energy from the tip of laser fiber 20 to maxillary ostium 14, to an obstruction in maxillary ostium 14, or to another desired treatment site in the sinus or in the vicinity of the sinus. For this purpose, laser fiber 20 can be moved axially and/or rotated in sheath 16, if desired.

Because the first and second openings are spaced apart along jawbone 12, laser fiber 20 can be moved transversely across the field of view provided through endoscope 22 which can be a valuable advantage to a surgeon or other user. Longitudinal viewing along the axis of a laser fiber or other surgical instrument while manipulating can be difficult. The possibility of lateral viewing provided by the invention can enhance depth judgment, enhance precise manipulation of the laser fiber and provide a better view of the ostium or other target site. Different locations and spacings along jawbone 12 can be selected to provide different views.

Also, the working instrument and the viewing instrument can readily be reversed, or swapped between sheaths 16 and 18 to simply provide a different angle of view, and a different angle of address of the working instrument to the work site or to address a new work site. This flexibility can be achieved without cutting or piercing a new opening.

The useful cross-sectional area of each surgical instrument for a given size of opening into the anatomy of the subject can be substantially larger than would be practicable with a dual lumen instrument deploying two instruments through a single opening.

The invention also can enable a wide range of working surgical instruments and procedures, including many known surgical instruments and procedures, to be deployed at an inaccessible sinus site and to be accompanied with effective illumination and visualization without the challenges of simultaneously introducing multiple instruments through a single surgical opening. Some suitable surgical instruments and procedures are described elsewhere herein.

One, or both, of the surgical instruments can be dual lumen instruments, if desired, enabling three or possibly more functionalities to be deployed simultaneously.

Figure 2:
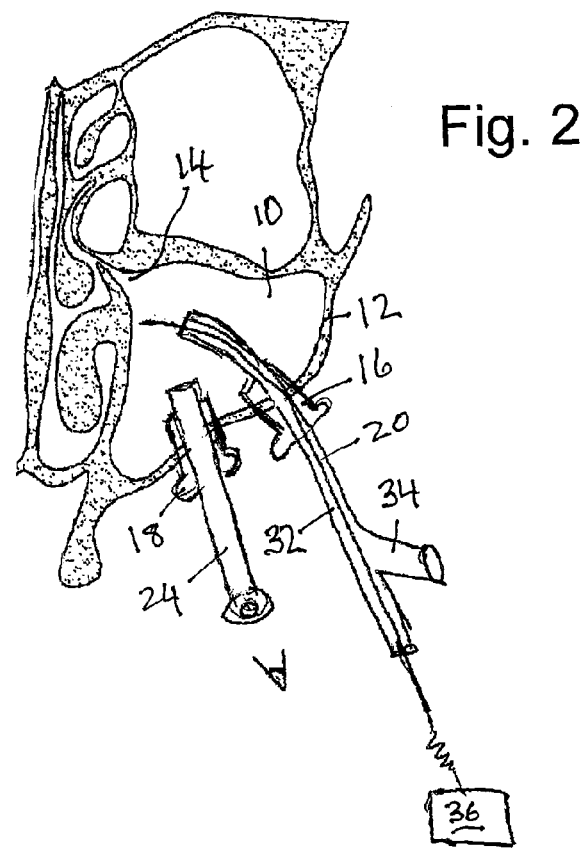
FIG. 2 is a view similar to FIG. 1 showing another embodiment of a system for performing sinus surgery according to the invention.

The surgical system and methodology illustrated in FIG. 2 are generally similar to the embodiment shown in FIG. 1. However, in FIG. 2, laser fiber 20 is shown inserted through a cannula 32, which can facilitate manipulation and orientation of laser fiber 20. Also cannula 32 can bring aspiration and/or irrigation to the work site via a side port 34. Laser fiber 20 is connected to a laser light source 36 of any suitable capacity and functionality, for example an energy capacity providing a power output at the tip in the range of from about 2 mW to about 20 w.

Figure 3:
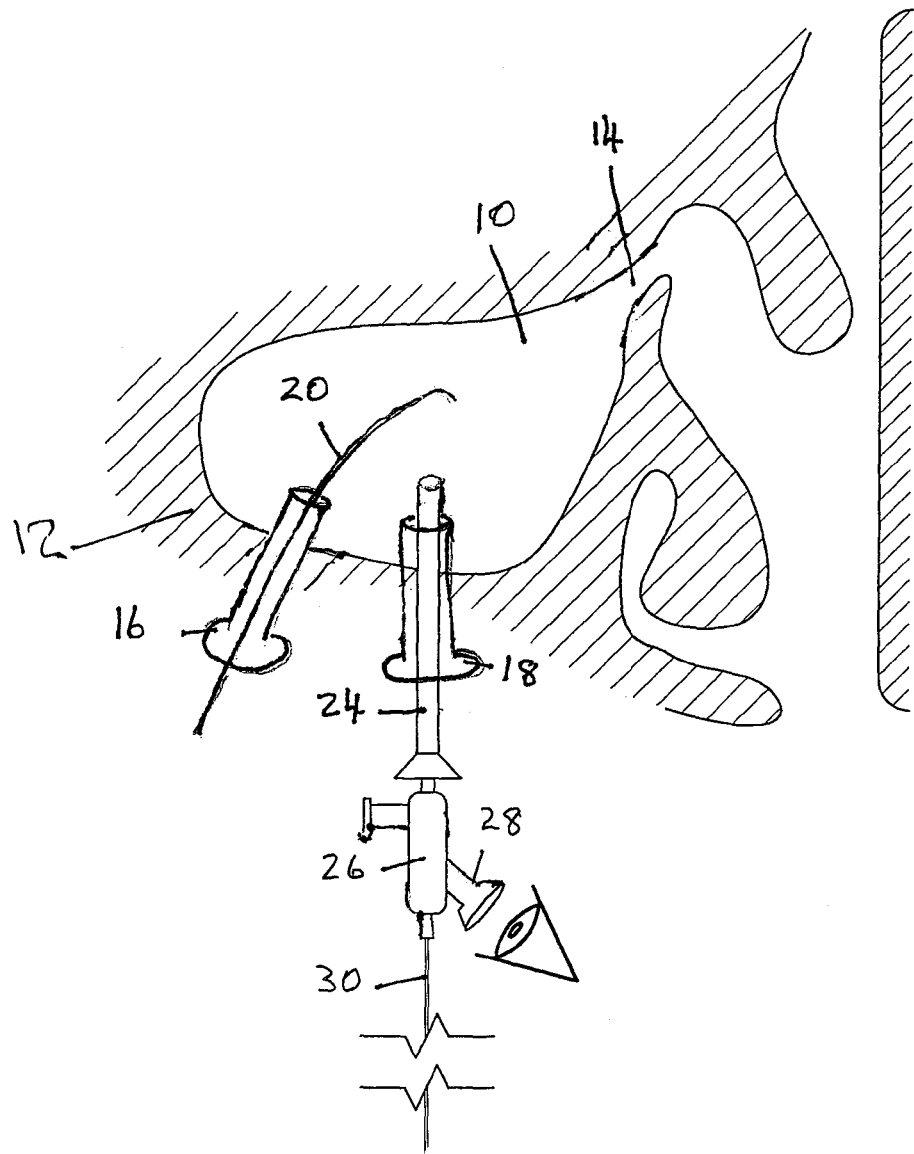
FIG. 3 is a coronal partial cross-sectional view of the left-hand maxillary sinus of another human subject, showing some of the soft tissues.

FIG. 3 shows a similar disposition of sheaths 16 and 18, laser fiber 20 and an endoscope 24 in the lefthand maxillary sinus of a subject. Endoscope 24 comprises a relatively complex optical system 26 which provides off-axis viewing through an eyepiece 28 and digital still or video imaging which can be output externally through a fiber 30.

Figure 4:
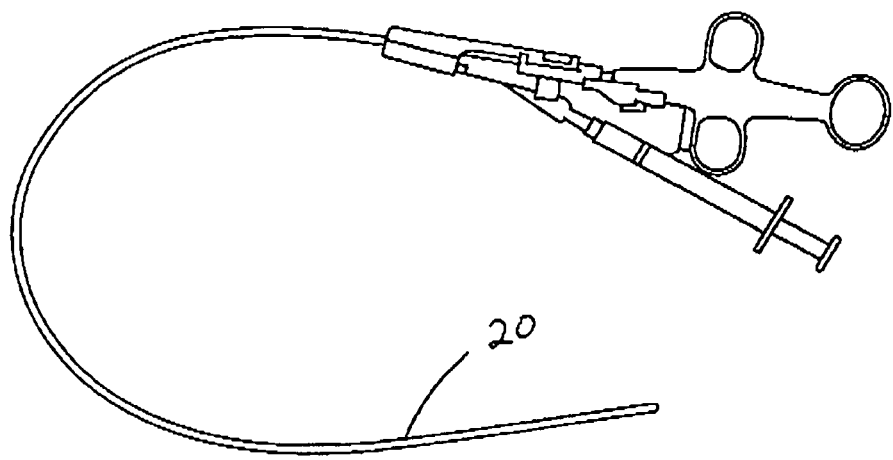
FIG. 4 shows a laser fiber manipulator useful in practicing the systems and methods of the invention.

A laser manipulator such as is shown in FIG. 4 can be employed to manipulate and provide auxiliary functionality to laser fiber 20, if desired. One useful example of the laser manipulator has a transverse diameter of about 2 mm accommodating two small and one large axial or longitudinal channels all of which are controllable by the surgeon, or other operator. One of the small passages can receive laser fiber 20 and the other can provide for evacuation of smoke generated by the laser. The large passage can be used for aspiration and/or irrigation. Syringe-style finger grips (uppermost in FIG. 4) permit the tip of the fiber to be manipulated through many different angulations. Thus, if desired, the tip can be rotated or bent into a desired configuration to address a particular treatment site or surface, for example the inside of the maxillary ostium.

Figure 5:
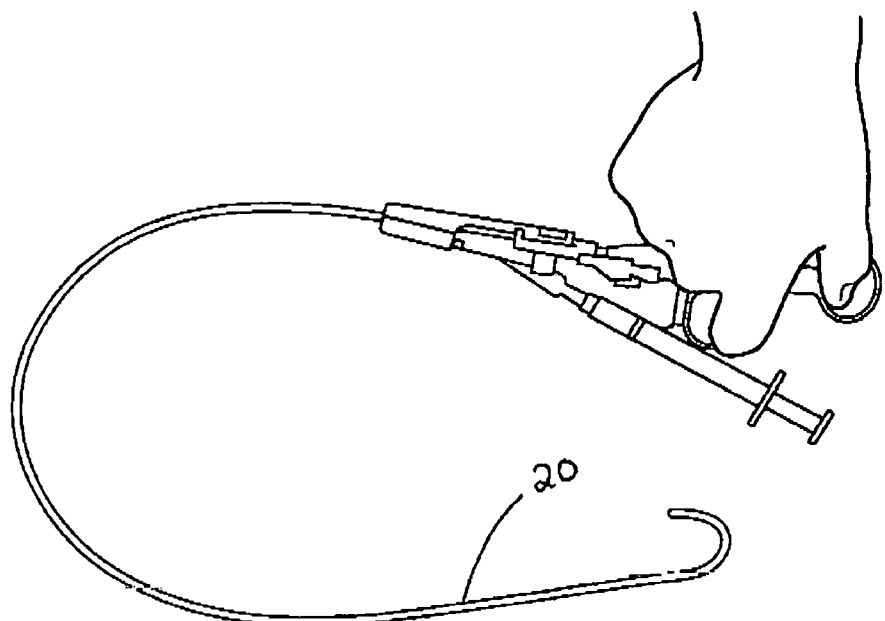
FIG. 5 illustrates one manner of manipulation of the laser fiber manipulator illustrated in FIG. 4.

FIG. 5 exemplifies a configuration into which the tip of laser fiber 20 can be manipulated with the laser manipulator shown in FIG. 4.

It will be understood that balloon dilatation procedures such as are described in US 2008-0172033 can advantageously be conducted through one of the openings provided by the present invention, using a single or dual lumen cannula, and employing a second opening in the anatomy pursuant to the invention, for visualization.

One embodiment of a method according to the invention comprises a method to treat inflammation of a sinus, or a sinus ostium, for example inflammation at, in, or near the maxillary sinus, or the maxillary ostium. This method can comprise piercing of first and second access openings into the anatomy of a patient and insertion of an endoscope or other illuminated viewing device through the first access opening, all as described herein. The method can further comprise inspecting the sinal mucous membrane through the endoscope for an indication of inflammation. When inflammation is indicated, the method can also include applying an anti-inflammatory treatment through the second access opening to the inflamed site.

Inspecting the sinal mucous membrane can comprise viewing the cilia and viewing or visualizing the ciliary flow of mucous through the sinus cavity, determining whether the ciliary flow is impaired and construing impaired ciliary flow as an indication of inflammation.

An anti-inflammatory treatment can be applied in any suitable manner. In one embodiment of the method, the anti-inflammatory treatment is effected by applying a suitable anti-inflammatory dosage of light through an optical fiber inserted through the second passageway, optionally by using a suitable light applicator instrument. The applied light can have one or more peak wavelengths in a range of from about 280 nm to about 700 nm, or can have other suitable characteristics.

In another embodiment of the method, the anti-inflammatory treatment is effected by applying a suitable anti-inflammatory dosage of an anti-inflammatory solution or gel comprising an effective dosage of a steroid or of another suitable anti-inflammatory agent. An anti-inflammatory wound healing gel or liquid can be employed, if desired. Any suitable wound-healing composition can be employed. For example, a useful wound-healing composition can comprise a blend of cations found naturally in the body, such as two or more cations selected from the group consisting of potassium, zinc, calcium, and rubidium. The cations can be formulated into a wound-healing composition with any other suitable materials, for example a mixture of polyethylene glycols, and, optionally, citric acid.

The anti-inflammatory liquid or gel can be applied in any suitable manner, for example, by insertion of a suitable applicator through the second passageway. One suitable applicator comprises a dilatable balloon which can be dipped in, or coated with, the anti-inflammatory liquid or gel and inserted through the second passageway employing a balloon dilation catheter. The balloon can be dilated in situ and applied to the tissue surface or surfaces to be treated, releasing a dosage of anti-inflammatory liquid or gel.

The anti-inflammatory treatment can be applied to any appropriate tissue or anatomical structure subject to inflammation, including the sinal mucosa and any associated sinus ostium, for example, tissue at, in, or near the maxillary sinus, or the maxillary ostium.

As with other procedures described herein, the anti-inflammatory treatment can be effected through the second passageway (or the first passageway) under visual supervision through the first passageway (or the second passageway).

Surgical Instruments.

Any suitable surgical instrument or combination of surgical instruments can be employed. Usefully, two surgical instruments can be employed simultaneously and one of these two instruments can be, but need not necessarily be, a visualization tool, for example an endoscope.

Any suitable endoscope can be employed in the practice of the invention. If desired, the endoscope can provide illumination, and optionally, direct viewing through one or more optical elements, imaging, video imaging, videography or recording of images, or computer processable image output, or any desired combination of these functionalities. Some examples of endoscopes that can be employed include but are not limited to rigid endoscopes, flexible endoscopes, digital video endoscopes with a digital chip at the tip end, zooming endoscopes, "contact endoscopes" with any desired magnification for example from 5× to 200× or more, including magnifications that can be used for examination of cells and ciliary function as a step in a method of the invention. Other viewing and/or illumination devices can also be employed, if desired.

Some examples of suitable surgical instruments include without limitation: a laser fiber, with or without a fiber diffuser or a balloon diffuser, a culture swab, an aspiration device for withdrawing fluid for culture, cytology or for both culture and cytology, a probe, a sensor, an ultrasound sensor, a gas saturation sensor, cottle elevator, sickle or straight knife, Blakesley, Takahashi, Grunwald-Henke, or Castelnuovo forceps, a backward biting punch, a circular cutting punch, a Kerrison punch, a suction tube, a cannula, an irrigation tube, a bipolar forceps, a Montgomery-Youngs clip applicator, a scissors, a dissector, or an elevator.

Some further surgical instruments which can be employed include:
- a flexible, fully articulated mini cup forceps useful, for example for biopsy and removal of bone and soft tissue;
- a cytology brush;
- a basket-type forceps for dilatation, removal of foreign bodies and snaring polyp-type structures, and other such useful procedures;
- use of a "Y" adapter to enable a one-channel instrument to be used for two different functions via two access channels to the sinus or other target site; and
- a micro drill passed through one of the openings for reducing sinus bony wall, the micro drill optionally having a flexible shaft to be introduceable thru flexible or soft-walled working channel.

The surgical instrument can be inserted with or without navigation. The described and other known or apparent uses or manipulations of the various surgical instruments and surgical tools described herein can also be employed in the methods of the invention.

Other suitable surgical instruments will be apparent to a person of ordinary skill in the art in light of this disclosure, or will become apparent to a person of ordinary skill in the art in the future, as the art develops.

Surgical Methods and Procedures.

Some examples of surgical procedures which can be performed employing one or more methods or systems according to the present invention, include, without limitation:
- treatment of lesions, for example by biopsy, ablation, excision or other suitable methods; debridement with a suitable device or devices;
- laser-assisted debridement; removal or ablation of maxillary sinus polyps and cysts without medial maxillary wall excision, optionally for treatment of cystic fibrosis;
- optical illumination for microbial reduction via optical fiber, or other suitable means, employing a laser or other suitable optical source, with or without one or more photo-activated agents;
- low intensity light therapy, optionally with a diffuser fiber, with or without photo-activated agent;
- irrigation or drainage for acute sinusitis of maxillary-ethmoid disease or maxillary disease, for cytologic or bacterial and/or fungal diagnosis, or other purposes relevant to treatment of the disease;
- controlled irrigation of the sinus cavity using an irrigation pump, optionally employing a suitable stream force to cleanse the sinus secretions without causing ciliary or mucosal damage;
- trans-antral ethmoid puncture, puncture of the ethmoid bulla, or complete ethmoidectomy and sphenoidotomy;
- control of epistaxis via direct coagulation using needle tip cautery or a laser, and/or by using clips or bipolar agents;
- introduction of one or more antimicrobials, antibiotics, antifungal, steroids or other suitable pharmacologic agent or chemical therapeutic agent locally to the sinus site or the vicinity of the sinus site, optionally by direct spray, injection, wash, drip or using a delivery or carrier device, for example a degradable or biodurable polymer which can be implanted in situ for any desired period, or can be removed promptly after delivering the carried treatment agent;
- placement of a stent or similar device, to remain temporarily or permanently in situ, to keep a sinus ostium patent, to provide postoperative care, or for other purposes;
- staining, evaluation and/or therapy for diagnosis and/or treatment of ciliary dysfunction in chronic rhinosinusitis or other diseases or conditions.

If desired the methods and procedures can be practiced employing robotic surgery and/or robotic or machine-controlled navigation of one or more surgical instruments or devices employed.

The foregoing surgical procedures and others described herein can be used individually or in some cases two or more can be combined together, as will be apparent to a person of ordinary skill in the art, or will become apparent in the future, as the art develops.

Any of the instruments, devices and methods described in United States Patent Application Nos. 2005/0107853, 2009/0054881 and 2008/0172033, the disclosures of which are each incorporated by reference herein, can be employed in practicing the present invention, if desired.

It will be understood that any desired combination of surgical instruments can be used to simultaneously access a target sinus site through the first and second openings into the subject's anatomy. In many cases, it can be desirable that one of the instruments is a visualization system.

Treatment at Other Sites.

While the invention has been described with reference to treatment of sinus sites, other sites which can be treated, and other procedures which can be employing utilizing one or more principles, systems, or devices of the invention will be apparent to a person of ordinary skill in the art, or will become apparent in the future, as the art develops in light of this disclosure. Some examples of such other sites and procedures include, without limitation:

eye and orbit sites;
trauma treatment of orbital wall fractures or the eye, for example, tri-malar fractures, optionally without external or orbital incision, for example, enabled or facilitated by expansion and suspension of a balloon, or other suitable device, placed in the maxillary sinus and not in the maxillary ostium;
ocular orbital decompression;
ocular infra-orbital nerve decompression;
pterygopalatine fossa access procedures including, without limitation, diagnostic biopsy for a tumor using needle aspiration, true cut needles, forceps, or another suitable method;
ligation or clipping of the sphenopalatine artery or branches thereof;
nerve access, for example, without limitation, vidian neurectomy or ablation using a laser, cryogenically, with RF, microwave, or other suitable radiation or method;
dental sites and procedures, for example, without limitation, oroantral fistule closure;
removal of dental or other foreign bodies or granulomas; and
insertion of brachytherapy catheters, or other devices for treatment of cancer;
augmenting partial maxillectomy; and
obtaining a mucosal graft, for bleeding control or septal perforation closure or other appropriate purpose.

Treatment of Nonhuman Mammals.

While the invention has been described in relation to the treatment of humans, it will be understood that the methods, principles, systems, instruments and apparatus of the invention can also be applied to non-human mammals including for example, horses, cattle, sheep and other husbanded animals, pets such as dogs and cats, laboratory animals for example mice, rats, rabbits, apes, monkeys and other primates, animals employed for sports, entertainment, law enforcement, draft usage, zoological or other purposes.

Disclosures Incorporated.

The entire disclosure of any United States patent or patent application, any foreign or international patent publication, of any other publication and of any unpublished patent application that is specifically referenced in this specification is hereby incorporated by reference herein, in its entirety. Should there appear to be conflict between the meaning of a term employed in the description of the invention in this specification and with the usage in material incorporated by reference from another document, the meaning as used herein is intended to prevail.

The foregoing detailed description is to be read in light of and in combination with the preceding background and invention summary descriptions wherein partial or complete information regarding the best mode of practicing the invention, or regarding modifications, alternatives or useful embodiments of the invention may also be set forth or suggested, as will be apparent to one skilled in the art. The description of the invention is intended to be understood as including combinations of the various elements of the invention, and of their disclosed or suggested alternatives, including alternatives disclosed, implied or suggested in any one or more of the various methods, products, compositions, systems, apparatus, instruments, aspects, embodiments, examples described in the specification or drawings, if any, and to include any other written or illustrated combination or grouping of elements of the invention or of the possible practice of the invention, except for groups or combinations of elements that will be or become apparent to a person of ordinary skill in the art as being incompatible with or contrary to the purposes of the invention.

Throughout the description, where instruments, devices apparatus or systems are described as having, including, or comprising specific components, or where processes or methods are described as having, including, or comprising specific process steps, it is contemplated that the instruments, devices apparatus, systems, processes or methods of the present invention can also consist essentially of, or consist of, the recited components, and that the processes of the present invention can also consist essentially of, or consist of, the recited processing steps. It should be understood that the order of steps or order for performing certain actions is immaterial so long as the invention remains operable. Moreover, two or more steps or actions may be conducted simultaneously. In addition, all proportions recited herein are to be understood to be proportions by weight, based upon the weight of the relevant composition, unless the context indicates otherwise.

While illustrative embodiments of the invention have been described above, it is, of course, understood that many and various modifications will be apparent to those of ordinary skill in the relevant art, or may become apparent as the art develops, in the light of the foregoing description. Such modifications are contemplated as being within the spirit and scope of the invention or inventions disclosed in this specification.

What is claimed is:

1. A method of sinus surgery for treating an inaccessible sinus site in a sinus of a human subject in need of sinus treatment, the method comprising:
    piercing a first access opening into the sinus of the human subject from a first externally accessible anatomical location to provide access to the inaccessible sinus site;
    piercing a second access opening into the sinus of the human subject from a second externally accessible anatomical location to provide access to the inaccessible sinus site;
    inserting a first surgical instrument, into the first access opening and traversing the first access opening with the first surgical instrument to introduce the first surgical instrument to the inaccessible sinus site, wherein the first surgical instrument comprises a source of illumination to illuminate a target site and a viewing device enabling the sinus site to be viewed externally of the human subject;
    inserting a second surgical instrument into the second access opening and traversing the second access opening with the second surgical instrument to introduce the second surgical instrument to the inaccessible sinus site;

cooperatively manipulating the first and second instruments while each instrument is introduced to the sinus site to perform a sinus treatment; and inspecting the sinus site through the first surgical instrument for an indication of inflammation and, responsive to inflammation being indicated, applying an anti-inflammatory treatment to the sinus site using the second surgical instrument through the second access opening.

2. A method according to claim 1 wherein the first accessible location and the second accessible location are sublabial sites.

3. A method according to claim 2 wherein both the first access opening and the second access opening extend into or through a maxillary antrum.

4. A method according to claim 1 wherein the first surgical instrument comprises an endoscope.

5. A method according to claim 1 wherein the first and second access openings are pierced so that the first and second openings are oriented to converge at or near the inaccessible sinus site.

6. A method according to claim 1 wherein an angle between the access openings is selected from the group of angles consisting of an acute angle, an angle in the range of from about 3° to about 60°, an angle in the range of from about 5° to about 30° and an angle in the range of from about 10° to about 20°.

7. A method according to claim 1 wherein the first access opening has a separation from the second access opening selected from the group consisting of: a separation of from about 1 mm to about 100 mm, a separation of from about 5 mm to about 50 mm; and a separation of from about 10 mm to about 30 mm.

8. A method according to claim 1 comprising piercing the first access opening or the second access opening or both the first and the second access openings with a piercing tool providing an opening having a greatest transverse dimension, in the range selected from the group consisting of from about 0.5 mm to about 5 mm and from about 1 mm to about 3 mm.

9. A method according to claim 8 wherein the first instrument comprises an endoscope having a transverse dimension of at least 3 mm when inserted into the subject and the piercing tool opening is at least 3 mm.

10. A method according to claim 1 wherein the method comprises inserting a first hollow sheath into the first access opening, inserting a second hollow sheath into the second access opening and inserting the first and second surgical instruments through the respective first and second sheaths into the respective first and second access openings.

11. A method according to claim 1 wherein the method comprises raising an upper lip of the human subject upwardly and piercing the first and second access openings in an upper gum.

12. A method according to claim 1 wherein the sinus treatment performed comprises a therapeutic or prophylactic treatment.

13. A method according to claim 1 wherein the anti-inflammatory treatment comprises applying an anti-inflammatory dosage of light through an optical fiber inserted through the second access opening.

14. A method according to claim 1 wherein the anti-inflammatory treatment comprises applying an anti-inflammatory dosage of an anti-inflammatory liquid or gel by insertion of a suitable applicator through the second access opening.

15. The method according to claim 14, wherein the suitable applicator comprises a dilatable balloon bearing a dosage of the anti-inflammatory liquid or gel.

16. The method according to claim 15, further comprising:
inserting the dilatable balloon through the second access opening.

\* \* \* \* \*